(12) United States Patent
Suh

(10) Patent No.: US 9,237,988 B2
(45) Date of Patent: Jan. 19, 2016

(54) BENZALKONIUM CHLORIDE COMPOSITIONS FOR INHIBITING THE HYDROLYTIC ACTIVITY OF ENDOGENOUS MATRIX METALLOPROTEINASES IN DENTAL RESTORATIONS

(75) Inventor: Byoung Suh, Oak Brook, IL (US)

(73) Assignee: Bisco, Inc., Schaumburg, IL (US)

( * ) Notice: Subject to any disclaimer, the term of this patent is extended or adjusted under 35 U.S.C. 154(b) by 210 days.

(21) Appl. No.: 12/932,397

(22) Filed: Feb. 24, 2011

(65) Prior Publication Data

US 2011/0207844 A1 Aug. 25, 2011

Related U.S. Application Data

(60) Provisional application No. 61/307,658, filed on Feb. 24, 2010.

(51) Int. Cl.
*A61K 6/083* (2006.01)
*A61K 6/00* (2006.01)

(52) U.S. Cl.
CPC ............ *A61K 6/0023* (2013.01); *A61K 6/0067* (2013.01); *A61K 6/083* (2013.01)

(58) Field of Classification Search
CPC ........ A61K 6/0067; A61K 6/08; A61K 6/083
USPC ........................................................ 523/118
See application file for complete search history.

(56) References Cited

U.S. PATENT DOCUMENTS

| 4,395,398 | A | * | 7/1983 | Yamamoto | 424/642 |
|---|---|---|---|---|---|
| 4,775,525 | A | | 10/1988 | Pera | |
| 5,385,728 | A | | 1/1995 | Suh | |
| 5,693,315 | A | | 12/1997 | Bevilacqua | |
| 6,472,454 | B1 | * | 10/2002 | Qian | 523/116 |
| 6,994,551 | B2 | | 2/2006 | Wang et al. | |
| 2003/0072781 | A1 | * | 4/2003 | Pelerin | 424/401 |
| 2003/0171450 | A1 | * | 9/2003 | Wang et al. | 523/115 |
| 2006/0193790 | A1 | | 8/2006 | Doyle et al. | |
| 2008/0182921 | A1 | * | 7/2008 | Suh et al. | 523/116 |
| 2009/0176891 | A1 | * | 7/2009 | Chogle et al. | 514/772.6 |
| 2010/0226998 | A1 | | 9/2010 | Fischer | |

OTHER PUBLICATIONS http://www.gdpdental.com/prod-tubulicidred.html (2003).
http://www.beutlich.com/documents/hurriseal/hurriseal-jada_2002_gordon_christensen.pdf (2002).
http://www.beutlich.com/documents/hurriseal/hurriseal_product_profile-dimensions_of_dental_hygiene_sept_2007.pdf (2007).
http://www.beutlich.com/documents/hurriseal/hurriseal_sell_sheet.pdf.
http://www.beutlich.com/documents/hurriseal/hurriseal_us_directions_handout.pdf.
http://www.beutlich.com/documents/hurriseal/msds_hurriseal_2008.pdf (2008).
http://www.beutlich.com/documents/hurriseal/quick_tips-nash_and_leinfelder.pdf (1999).
http://www.beutlich.com/documents/hurriseal/solutions_for_post-operative_sensitivity-ross_nash.pdf (1999).

* cited by examiner

*Primary Examiner* — Michael Pepitone
(74) *Attorney, Agent, or Firm* — Ice Miller LLP

(57) ABSTRACT

The present application relates to dental adhesive and restoration compositions comprising benzalkonium chloride, having the general structure $C_6H_5CH_2N(CH_3)_2$—R—Cl, and salts thereof in a range between approximately 0.01% and approximately 10% by weight in dental primer, dental adhesive, dental resin, and other dental polymeric compositions or in dental solutions. In particular, it has been shown that dental compositions comprising benzalkonium chloride result in the inhibition of the hydrolytic activity of MMP on the dentin adhesive layer, thereby reducing the degradation of bond strength between a resulting dental restoration and the underlying dental tissue.

12 Claims, No Drawings

BENZALKONIUM CHLORIDE COMPOSITIONS FOR INHIBITING THE HYDROLYTIC ACTIVITY OF ENDOGENOUS MATRIX METALLOPROTEINASES IN DENTAL RESTORATIONS

This application claims the benefit of U.S. Provisional Application No. 61/307,658, filed Feb. 24, 2010, which is hereby incorporated by reference in its entirety.

BACKGROUND

The groundwork for a successful dental restoration lies in the ability of the restoration to bond to the underlying tooth surface. One key to creating a successful bond between the tooth surface and a polymer based dental restoration is to create a strong bond at the hybrid layer between the collagen fibrils of the dentin and the dental polymer forming the restoration. In creating such a hybrid layer, acidic compositions, such as phosphoric acid etchants are used to expose the collagen fibers at the dentin-adhesive interface.

However, it has been reported that a degradation of the dentin-adhesive interface occurs over time due in large part to the hydrolytic activity of endogenous matrix metalloproteinases ("MMPs"). Carrilho et al, J. Dent. Res. 86(1):90-94 (2007). MMPs are zinc- and calcium-dependent proteolytic enzymes that are present within the intact dentin matrix, and which may be released from mineralized dentin matrix through acid-induced demineralization, such as through the use of etchants during preparation of the tooth surface during a dental restoration. Mazzoni et al., Biomaterials 27:4470-4476 (2006). In particular, it has been reported that specific MMPs, including MMP-2, MMP-8, and MMP-9 that exist within the dentin migrate into the hybrid layer and contribute to collagenolytic and gelatinolytic activity that results in the progressive reduction in resin-dentin bond strength, causing an ongoing weakening of the restoration nearly from the time the dental practitioner secures the restoration. Id.

As such, various known MMP inhibitors have been utilized, including the use of benzamidine HCl and chlorhexadine compositions in acid conditioners to wash tooth preparations and inhibit the hydrolytic activity of MMPs that may migrate into the hybrid layer. Further, the use of these MMP inhibitors in acid washes results in the clinical removal of the composition when the acid etchant is rinsed approximately 15 seconds after its application. Carrilho et al, J. Dent. Res. 86(1):90-94 (2007). Additionally, it is well known that the use of chlorhexadine can result in the staining of dental tissues, resulting in an unacceptable restoration. See, e.g., U.S. Pat. Nos. 5,385,728; 4,839,158. As such, an improved method and compositions for inhibiting the hydrolytic reactivity of MMPs in the hybrid layer would be greatly appreciated.

SUMMARY OF THE INVENTION

Compositions for use in dental restorations are disclosed that have reduced degradation by endogenous matrix metalloproteinases, that comprise a polymeric dental material and a benzalkonium chloride or a salt thereof in an amount ranging from approximately 0.01% to approximately 5% by weight. In a preferred embodiment, the polymeric dental material comprises a first component comprising ethanol, an amino acid or its salt derivative, and benzalkonium chloride or a salt thereof, and a second component comprising a polymerizable acidic monomer, a hydrophobic resin, a crosslinking monomer, a hydrophilic monomer, and a polymerization initiator.

In a particularly preferred embodiment, the composition is incorporated in a system comprising a primer/adhesive comprising a benzalkonium chloride or a salt thereof in an amount ranging from approximately 0.01% to approximately 5% by weight, and a hydrophobic dentin/enamel resin.

In an alternative embodiment, the composition comprises a solvent and a benzalkonium chloride or a salt thereof in an amount ranging from approximately 0.01% to approximately 10% by weight.

DETAILED DESCRIPTION OF THE INVENTION

According to the present invention, improved dental adhesive, washes, and restoration compositions are disclosed. In particular, it has been found that use of benzalkonium chloride, having the general structure $C_6H_5CH_2N(CH_3)_2$—R—Cl and salts thereof (where R is $(C_nH_{2n+1})$ and n=8 to 18), in a range between approximately 0.01% and approximately 10% by weight shows inhibition of MMPs and/or MMP hydrolytic activity. Accordingly the present application relates to the use of benzalkonium chloride, having the general structure $C_6H_5CH_2N(CH_3)_2$—R—Cl and salts thereof in a range between approximately 0.01% and approximately 10% weight percentage in solvents selected from a group consisting of water, ethanol, acetone or combinations thereof or other suitable liquids that do not adversely effect the dentin and other tooth structure or surrounding tissue of the patient as a separate step in the treatment of the patient (collectively "benzalkonium chloride dental solutions".) It is also presently expected that benzalkonium chloride combined in a range between approximately 0.01% and approximately 5% weight percentages in flowable dental materials such as dental primers, dental adhesives, dental resins, and other dental polymeric compositions (all collectively, "benzalkonium chloride dental materials") will provide similar beneficial MMP inhibition results when applied to the tooth or other components of the restorative process with or without a prior or subsequent application of benzalkonium chloride dental solutions. According to at least one presently contemplated embodiment, a benzalkonium dental solution or material operable to inhibit the hydrolytic activity of MMPs comprises benzalkonium chloride in a range of approximately 0.02% to approximately 2% by weight of the dental material. According to yet another embodiment, a dental solution operable to inhibit the hydrolytic activity of MMPs comprises benzalkonium chloride in a range of approximately 0.01 to approximately 5% by weight of the dental solution. According to yet other embodiments, a dental solution operable to inhibit the hydrolytic activity of MMPs comprises benzalkonium chloride in a range of approximately 0.2% to approximately 4% by weight, and a dental material comprises benzalkonium chloride in a range of approximately 0.02% to approximately 1%.

It will be appreciated that the use of a dental material comprising a polymerizable component that is relatively hydrophilic before polymerization of the system and is relatively hydrophobic after polymerization of the system, when combined with benzalkonium chloride or salts thereof in concentrations as set forth above are anticipated to be particularly effective, as the hydrophilic nature of the unpolymerized dental material results in deep penetration of the composition into the hybrid layer, thereby reducing any voids between the mineralized dentin and the adhesive/collagen interface, and allowing the MMP inhibitory action of the dental material comprising benzalkonium chloride to prevent the hydrolytic degradation of the bond between the dental tissue and the dental restoration.

Example I

In particular, it is presently expected that when benzalkonium chloride or a salt thereof is added at a concentration of about 0.02% to about 2% by weight to a primer/adhesive system comprising a first primer component A comprising ethanol and an amino acid salt derivative N(p-tolyl)glycine glycidyl methacrylate magnesium salt ("Mg NTG-GMA") and a second primer component B comprising polymerizable acidic monomer BPDM (biphenyl dimethacrylate), a crosslinking monomer dipentaerythritol pentaacrylate ("DPEPA"), the relatively hydrophobic resin bisphenol A glycidyl methacrylate ("BisGMA") or ethoxylated BisGMA, and initially hydrophilic monomer 2-hydroxyethyl-methacrylate ("HEMA"), and a polymerization initiator camphorquinone ("CQ") is expected to create an effective hybridization layer that shows reduced degradation from MMP interaction due to the MMP inhibitory effect displayed by benzalkonium chloride.

In one presently contemplated embodiment, a system for dental restorations comprises a hydrophobic dentin/enamel resin that is applied over a tooth surface prepared and primed with the primer/adhesive system described above. For example, a hydrophobic dentin/enamel resin may comprise BisGMA, urethane dimethacrylate ("UDMA"), triethyleneglycol dimethacrylate ("Tri-EDMA"), ethyl 4-dimethylaminobenzoate ("EDMAB"), CQ, and 4-methoxyphenol ("MEHQ").

It has also been found that removal of monomers such as HEMA from the resin, while including such a hydrophilic monomer in the primer, results in a high initial bond strength with improved long term bond strength.

Example II

For example, according to another presently expected exemplary embodiment, a primer/adhesive system comprises a part A comprising from approximately 90-99% (by weight) ethanol approximately 1%-10% (by weight) of an amino acid or its salt derivative such as Mg NTG-GMA, and approximately 0.01%-4% benzalkonium chloride; and a part B comprising a polymerizable acidic monomer such as BPDM at about 5%-30% (by weight), about 10%-40% HEMA (by weight), about 5%-15% DPEPA (by weight), about 20%-60% (by weight) of relatively hydrophobic resin BisGMA or ethoxylated BisGMA, and about 0.1%-1% CQ (by weight). According to one exemplary embodiment, Part B may comprise a polymerizable acidic monomer such as BPDM in an amount about 10% (by weight), about 38% HEMA (by weight), about 10% DPEPA (by weight), about 41% (by weight) of relatively hydrophobic resin BisGMA or ethoxylated BisGMA, about 0.5% CQ (by weight), and about 0.5% EDMAB (by weight). Additionally, a hydrophobic resin may comprise approximately 20-30% BisGMA (by weight), approximately 20-30% UDMA (by weight), approximately 30-47.77% Tri-EDMA (by weight), approximately 1.00-1.75% EDMAB (by weight), approximately 0.30-0.45% camphorquinone (by weight), and approximately less than 0.1% MEHQ (by weight).

Example III

According to another presently expected one exemplary embodiment of the present application, multiple benzalkonium chloride dental solutions were prepared in aqueous solutions in concentrations varying from 0.02% to 2%, and were incubated with MMP-9 enzymes for 4 hours. After both 1 and 4 hours of incubation, standard negative and positive controls were compared to the below concentrations of the test compositions using an Anaspec SensoLyte Generic MMP Assay Kit (#72095, Anaspec, Fremont, Calif., USA), with the resulting MMP inhibitions shown in Tables 1 and 2 below. It will be appreciated that benzalkonium chloride dental solutions at a concentration as low as 0.02% by weight displayed MMP inhibition, with concentrations as low as 0.5% displaying at least 85% MMP inhibition after 4 hours. Further, it should be noted that concentrations of 0.5% displayed 96% MMP inhibition within the first hour of incubation, indicating significant MMP inhibition during the time that would correspond to the initial clinical placement of a dental restoration in a prepared tooth surface.

TABLE 1

Percent Inhibition of MMP after Incubation with Benzalkonium Chloride (BAC)

| Percent benzalkonium chloride ("BAC") (by weight) | Percent MMP Inhibition at 1 Hour |
|---|---|
| 0.02% BAC | 0% |
| 0.05% BAC | 0% |
| 0.5% BAC | 96.5% |
| 1.0% BAC | 98.3% |
| 2.0% BAC | 100% |

TABLE 2

Percent Inhibition of MMP after Incubation with Benzalkonium Chloride

| Percent benzalkonium chloride ("BAC") (by weight) | Percent MMP Inhibition at 4 Hours |
|---|---|
| 0.02% BAC | 3% |
| 0.05% BAC | 6% |
| 0.5% BAC | 85% |
| 1.0% BAC | 95% |
| 2.0% BAC | 100% |

Although the invention has been described in detail with reference to preferred embodiments, variations and modifications exist within the scope and spirit of the invention as described and defined in the following claims.

What is claimed is:

1. A polymeric dental material for use in dental restorations having reduced degradation by endogenous matrix metalloproteinases, the polymeric dental material formed of a polymerized composition comprising:
   a first component comprising approximately 90%-99% by weight ethanol, approximately 1%-10% by weight N(p-tolyl)glycine glycidyl methacrylate magnesium salt, and a benzalkonium chloride or a salt thereof in an amount ranging from greater than 0.5% to approximately 2% by weight of the composition; and
   a polymerizable second component comprising about 5%-30% by weight biphenyl dimethacrylate, about 20%-60% by weight of bisphenol A glycidyl methacrylate (BisGMA) or ethoxylated BisGMA, about 5%-15% by weight of dipentaerythritol pentaacrylate, about 10%-40% by weight of 2-hydroxyethyl-methacrylate, and about 0.1%-1% by weight of a polymerization initiator.

2. The polymeric dental material of claim 1, wherein the polymeric dental material is selected from the group consisting of: a dental primer, a dental adhesive, a dental resin, and combinations thereof.

3. The polymeric dental material of claim 1, wherein the polymerization initiator is camphorquinone.

4. The polymeric dental material of claim 3, wherein the polymerizable second component comprises about 10% by weight biphenyl dimethacrylate, about 41% by weight bisphenol A glycidyl methacrylate (BisGMA) or ethoxylated BisGMA, about 0.5% by weight ethyl 4-dimethacrylate, about 10% by weight dipentaerythritol pentaacrylate, about 38% by weight 2-hydroxyethyl-methacrylate, and about 0.5% by weight camphorquinone.

5. A system for dental restorations having reduced degradation by endogenous matrix metalloproteinases, comprising:
a primer/adhesive having a first component comprising approximately 90%-99% by weight ethanol, approximately 1%-10% by weight N(p-tolyl)glycine glycidyl methacrylate magnesium salt, and a benzalkonium chloride or a salt thereof in an amount ranging from greater than 0.5% to about 2% by weight; and a second component comprising about 5%-30% by weight biphenyl dimethacrylate, about 20%-60% by weight bisphenol A glycidyl methacrylate, about 5%-15% by weight dipentaerythritol pentaacrylate,) about 10%-40% by weight 2-hydroxyethyl-methacrylate, and about 0.1%-1% by weight of a polymerization initiator; and
a hydrophobic dentin/enamel resin applied over the primer/adhesive.

6. The system of claim 5, wherein the polymerization initiator is camphorquinone.

7. The system of claim 5, wherein the hydrophobic dentin/enamel resin comprises bisphenol A glycidyl methacrylate, urethane dimethacrylate, triethylene dimethacrylate, ethyl 4 dimethylaminobenzoate, camphorquinone, and 4-methoxyphenol.

8. The system of claim 7, wherein:
the hydrophobic dentin/enamel resin comprises approximately 20%-30% by weight bisphenol A glycidyl methacrylate, approximately 20%-30% by weight urethane dimethacrylate, approximately 30%-47.77% by weight triethylene dimethacrylate, approximately 1.00%-1.75% by weight ethyl 4 dimethylaminobenzoate, approximately 0.30%-0.45% by weight camphorquinone, and approximately less than 0.1% by weight 4-methoxyphenol.

9. The system of claim 8, wherein the primer adhesive has a second component comprising about 10% by weight biphenyl dimethacrylate, about 41% by weight bisphenol A glycidyl methacrylate (BisGMA) or ethoxylated BisGMA, about 0.5% by weight ethyl 4-dimethylaminobenzoate, about 10% by weight dipentaerythritol pentaacrylate, about 38% by weight 2-hydroxyethyl-methacrylate, and about 0.5% by weight camphorquinone.

10. The system of claim 5, wherein the hydrophobic dentin/enamel resin does not contain a hydrophilic monomer.

11. The system of claim 5, wherein the benzalkonium chloride or a salt thereof is in an amount between about 1% to about 2% by weight.

12. The polymeric dental material of claim 1, wherein the benzalkonium chloride or a salt thereof is in an amount between about 1% to about 2% by weight of the composition.

\* \* \* \* \*